United States Patent [19]
Harmon

[11] Patent Number: 5,470,861
[45] Date of Patent: Nov. 28, 1995

[54] METHOD OF PROMOTING HAIR GROWTH

[75] Inventor: Charles S. Harmon, Bloomfield, N.J.

[73] Assignee: Hoffmann-La Roche Inc., Nutley, N.J.

[21] Appl. No.: 286,152

[22] Filed: Aug. 4, 1994

[51] Int. Cl.⁶ .................................... A61K 31/44
[52] U.S. Cl. ......................................... 514/337
[58] Field of Search .............................. 514/337

[56] References Cited

U.S. PATENT DOCUMENTS

| | | | |
|---|---|---|---|
| 4,971,982 | 11/1990 | Attwood et al. | 514/337 |
| 5,028,711 | 7/1991 | Stenzel et al. | 546/196 |

FOREIGN PATENT DOCUMENTS

| | | |
|---|---|---|
| 9056007 | 12/1990 | Australia . |
| 9059751 | 1/1991 | Australia . |
| 9058725 | 1/1991 | Australia . |
| 9060134 | 2/1991 | Australia . |
| 9065644 | 5/1991 | Australia . |
| 0350805 | 7/1989 | European Pat. Off. . |
| 0400430 | 5/1990 | European Pat. Off. . |
| 0406656A1 | 6/1990 | European Pat. Off. . |
| 0410208A1 | 7/1990 | European Pat. Off. . |
| 0427606A1 | 11/1990 | European Pat. Off. . |
| 3926001A1 | 5/1989 | Germany . |
| 2204868 | 5/1988 | United Kingdom . |
| WO86/00616 | 1/1986 | WIPO . |
| 88/00822 | 2/1988 | WIPO . |
| WO92/14439 | 3/1992 | WIPO . |

OTHER PUBLICATIONS

Uno, et al. Cyclic Dynamics of Hair Follicles and Effect of Minoxidil on the Bald Scalps of Stumptailed Macaques, The American Journal of Dermatology 7(3):283–297 (1985).

Uno, et al. Stumptailed Macaques as a Model of Male Pattern Baldness Models Dermatol. vol. 3 pp. 159–169 (1987).

Uno, H., The Stumptailed Macaque as a Model for Baldness: Effects of Minoxidil, International Journal of Cosmetic Science 8, 63–71 (1986).

Abstract (Corresponding to WO 9214439) 1992.

Primary Examiner—Raymond Henley, III
Assistant Examiner—Phyllis G. Spivack
Attorney, Agent, or Firm—George M. Gould; George W. Johnston; Ellen Ciambrone Coletti

[57] ABSTRACT

The use of the compound 2-(6-cyano-3,4-dihydro-2,2-dimethyl-2H-1-benzopyran-4-yl)pyridine-1-oxide represented by the formula

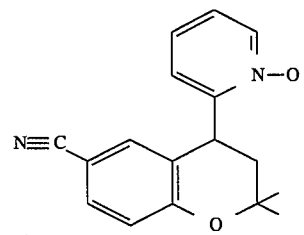

as well as pharmaceutically acceptable salts, as topical agents to promote hair growth is disclosed.

19 Claims, No Drawings

METHOD OF PROMOTING HAIR GROWTH

BACKGROUND OF THE INVENTION

Hair loss or alopecia, is a common affliction of humans. The most common form of hair loss in both males and females is pattern baldness or androgenic alopecia.

Hair follicles range in size from small, superficial, vellus follicles to large, deep, terminal follicles. The cyclic growth phases of hair follicles are telogen (resting), anagen I–III (developing), anagen IV–VI (growing) and catogen (involuting). Uno, et al., *Cyclic Dynamics of Hair Follicles and the Effect of Minoxidil on the Bald Scalps of Stumptailed Macaques,* The American Journal of Dermatopathology, 7(3):283–297 (1985).

In the development of androgenic alopecia there is a gradual diminution of follicle size, with conversion of large, terminal follicles producing thick, pigmented hair fibers (terminal hairs) to small, vellus follicles producing fine non-pigmented hair fibers (vellus hairs). In addition, the proportion of growing anagen follicles declines.

It has been found that the compound, 2-(6-cyano-3,4-dihydro- 2,2-dimethyl-2H-1-benzopyran-4-yl)pyridine-1-oxide stimulates the conversion of vellus hair to terminal hair and increases the growth of terminal hair thereby promoting hair growth.

SUMMARY OF THE INVENTION

In accordance with this invention, the compound 2-(6-cyano-3,4-dihydro-2,2-dimethyl-2H-1benzopyran-4-yl)pyridine-1-oxide, represented by the formula

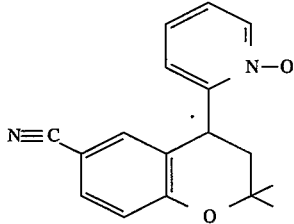

as well as pharmaceutically acceptable salts of this compound, applied topically to the skin of a host stimulates hair growth.

In another aspect, the compound of Formula I increases the rate of terminal hair growth and stimulates the conversion of vellus hair to terminal hair.

DETAILED DESCRIPTION OF THE INVENTION

The invention relates to a method for promoting hair growth including promoting hair growth in a host afflicted with androgenetic alopecia, which comprises topically administering to a host in need of such promotion an effective amount of 2-( 6-cyano-3,4-dihydro-2,2-dimethyl-2H-1benzopyran-4 -yl)pyridine-1-oxide, represented by the formula

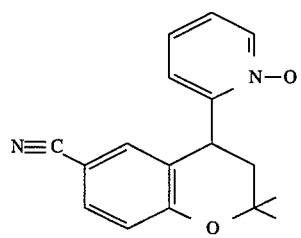

as well as pharmaceutically acceptable salts of the compound of formula I.

In another aspect, the invention relates to a method of increasing the rate of terminal hair growth and stimulating the conversion of vellus hair to terminal hair by topically administering to a host in need of such stimulation an effective amount of the compound of formula I.

A process for preparing the compound 2-(6-cyano-3,4-dihydro-2,2-dimethyl-2H-1-benzopyran-4-yl)pyridine-1-oxide, represented by the formula

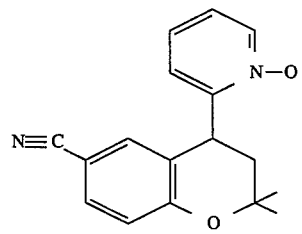

is set forth in U.S. Pat. No. 4,971,982, issued Nov. 20, 1990, which is hereby incorporated by reference.

The compound of formula I, when applied topically to the skin, promotes hair growth. The compound of formula I should be applied to that portion or area of the skin which is affected by hair loss or in which treatment is desired.

The compound of formula I can be applied in accordance with this invention to skin in conventional topical compositions. These compositions can be utilized to apply the compound of formula I to the skin and body, particularly the head. The preferred method of application of the compound of formula I, topically to produce the best effects should start soon after the onset of alopecia. Thereafter, this composition can be continuously applied to a host to promote hair growth.

The compound of formula I can be administered in accordance with this invention in any conventional suitable topical preparation, for example, in combination with any suitable conventional carrier useful for topical administration. Therefore, the compound of formula I can be administered in accordance with this invention in any suitable topical composition such as a cream, ointment, soap, gel, solution, lotion, shampoo and the like. Generally, for most efficacious results, these topical compositions contain at least 0.0005% by weight of the total composition of the compound of formula I, preferably from about 0.0005% to about 5% by weight of the total composition of the compound of formula I with amounts of from 0.05% to 5% by weight of the total composition being especially preferred. Particularly preferred is a topical composition comprising from about 1% to about 5% by weight of the compound of formula I. If desired, higher concentrations may be utilized depending upon the nature and extent of desired hair growth.

The method preferably comprises topically administering 50 mg of the compound of formula I per day to an adult human.

In formulating these compositions, any conventional nontoxic, dermatologically acceptable base or carrier in which the compound of formula I is stable can be utilized. The preferred compositions of the invention are solutions. The topical compositions of this invention can, if desired, contain suitable sunscreen agents. Any conventional sunscreen agent can be utilized in formulating the formulations containing the compound of formula I which can be utilized in accordance with this invention.

These topical compositions which contain the compound of formula I can contain any of the conventional excipients and additives commonly used in preparing topical compositions. Among the conventional additives or excipients, which can be utilized in preparing these compositions in accordance with this invention are preservatives, thickeners, perfumes and the like. In addition, the conventional antioxidants, such as butylated hydroxyanisoles (BHA), ascorbyl palmitate, propyl gallate, sodium ascorbate, citric acid, butylated hydroxy toluene (BHT), ethoxyquin, tocopherol, and the like can be incorporated into these compositions. These topical compositions can contain conventional acceptable carriers for topical applications which are generally utilized in these compositions. These compositions may contain chelating agents, solubilizing agents, neutralizing agents, buffering agents, thickening agents, humectants, emulsifying agents, skin and hair conditioners, and viscosity stabilizers, such as those generally utilized. In addition, these compositions can contain colorants, and perfumes which are conventional in preparing cosmetic compositions.

The hair conditioners may be, for example, lanolin and lanolin derivatives, hydrolyzed animal protein and alkyamidopropyl dimethyl 2,3-dihydroxy-propyl ammonium chloride.

The viscosity agent may be an alcohol selected from the group consisting of cetyl alcohol, stearyl alcohol, ceteostearyl alcohol, and myristyl alcohol. The viscosity agent may also be xanthan gum, a magnesium aluminum silicate such as veegum or carbomer, hydroxyethylcellulose, cellulose gum or hydroxypropylcellulose, glyceryl stearate, hydrogenated castor oil, cetyl palmitate, stearic acid; a combination of synthetic and semisynthetic wax; a combination of glyceryl stearate, cetearyl alcohol, cetyl palmitate and cocoglycerides blend; or a combination of glyceryl hydroxystearate, cetyl palmitate and trihydroxystearin blend. The viscosity agent may also be two or more of any of the viscosity agents mentioned above.

The hydrophilic solubilizer can be dimethyl isosorbide, propylene glycol or transcutol; or an aliphatic alcohol selected from the group consisting of ethyl alcohol, isopropyl alcohol, polyethylene glycol, or more preferably ethyl alcohol.

The lipophilic solubilizer can be castor oil; isopropyl myristate; an alcohol selected from the group consisting of octyl dodecanol, isocetyl alcohol, oleyl alcohol, oleyl cetyl alcohol, or triglycerides of medium chain length vegetable fatty acids such as Miglyols® (manufactured by Huls of America) which are mixtures of caprylic and capric triglyceride, propylene glycol dicaprylate and dicaprate, or a mixture of caprylic and capric triglyceride; or Neobee M-5. The lipophilic solubilizers more preferably are triglycerides of medium chain length vegetable fatty acids such as Miglyols®.

The emulsifier can be a polysorbate selected from the group consisting of Polysorbate 20, Polysorbate 40, Polysorbate 60 and Polysorbate 80; a sorbitan selected from the group consisting of sorbitan laurate, sorbitan oleate, sorbitan palmitate, sorbitan stearate, sorbitan trioleate or sorbitan tristearate. The emulsifier can also be glyceryl monostearate, polyoxyethylene stearate, polyoxyethylene lauryl ether, PEG- 20 glyceryl stearate, ceteareth-12, ceteareth-20, ceteareth-30, PPG-2-Ceteareth-9, polyethylene glycol ethers of oleyl alcohol such as oleth-5, oleth 10, a mixture of oleth-5 and oleth-10, sterols such as soya sterol, PEG-5 soya sterol, PEG-10 sterol, PEG-16 soya sterol, PEG-25 soya sterol, and also the emulsifier can be sodium cetearyl sulfate, or PEG-40 hydrogenated castor oil.

The emollient can be an ester such as oleyl oleate, octyl stearate, myreth-3 myristate, hexyl laurate, dibutyl adipate, isocetyl stearate, octyldodecyl stearate, PEG-7-glyceryl cocoate, oleyl erucate, a mixture of coco-caprylate and caprate, myristal myristate, cetearyl isonanoate, decyl oleate, a mixture of caprylic and capric triglyceride, PEG-5-Laureth-5, trihydroxymethoxy stearin, and a mixture of propylene glycol dicaprylate and dicaprate. The emollient can also be castor oil or dioctyl cyclohexane, mineral oil or silicone oil.

The preservative can be cis-1-(3-chloroethyl)-3,5,7-triaza-1-azoniaadamantane chloride; sorbic acid; potassium sorbate; benzyl alcohol; benzalkonium chloride; dichlorobenzyl alcohol; N-(hydroxymethyl)-N-(1,3-dihydroxymethyl-2,5 -dioxo-4-imidazolidinyl)-N-hydroxymethyl)urea; boric acid; chlorobutanol; monothioglycerol; methyl paraben; propyl paraben.

The chelating agent can be salts of ethylenediamine tetraacetic acid (EDTA), dimercaprol, ascorbic acid, citric acid, diphenylthiocarbazone, versene acid, or salts thereof, preferably salts of ethylenediamine tetraacetic acid (EDTA).

The humectant can be glycerin, propylene glycol, sodium 2-pyrrolidone-5-carboxylic acid (sodium PCA), hyaluronic acid.

The topical compositions containing the compound of formula I can be applied to the skin and should be preferably applied to the skin at least once a day. Compositions which contain the compound of formula I should be applied continually to promote hair growth. These preparations can be applied according to the need of the patient as determined by the prescribing physician. In any event, the particular regimen for application of this composition to a patient will typically depend on the age and degree of hair loss of the individual.

The invention is further illustrated in the following examples. These examples are for illustration and are not limitive of the claimed invention.

EXAMPLE 1

406 mg of m-chloroperbenzoic acid were added to a solution of 528 mg of 3,4-dihydro-2,2-dimethyl-4-(2-pyridyl)-2H-1 -benzopyran-6-carbonitrile in 15 ml of dichloromethane at room temperature. After 2 hours at room temperature, the mixture was washed with sodium bicarbonate solution and the organic phase was dried over sodium sulphate and evaporated. The residue was crystallized from t-butyl methyl ether and was recrystallized from toluene to give 360 mg of 2-(6-cyano- 3,4-dihydro-2,2-dimethyl-2H-1-benzopyran-4-yl)pyridine N-oxide of melting point 158°–160° C.

The 3,4-dihydro-2,2-dimethyl-4-(2-pyridyl)-2H-1-benzopyran- 6-carbonitrile used as the starting material was prepared as follows:

2.96 g of 2,2-dimethyl-4-(2-pyridyl)-2H-1-benzopyran-6-carbonitrile were dissolved in 100 ml of ethanol and added at room temperature to 100 mg of 10% palladiumon-charcoal. The mixture was shaken at room temperature under a hydrogen atmosphere for 2 hours. The catalyst was then removed by filtration and the filtrate was evaporated. The residue was chromatographed on silica gel using ethyl acetate/petroleum ether(1:2) for the elution. There were obtained 2.44 g of 3,4-dihydro-2,2-dimethyl-4-(2-pyridyl)-2H- 1-benzopyran-6-carbonitrile of melting point 114°–115° C.

EXAMPLE 2

Effect of Compound of Formula I on Hair Growth in Balding Stumptailed Macaques

The frontal alopecia that develops in post-adolescent stumptailed macaques has frequently been cited as a useful animal model for the study of human male-pattern baldness. Uno, et al., *Stumptailed Macaques as a Model of Male Pattern Baldness,* Models Dermatol. Vol. 3 pp. 159–169 (1987).

Method

Adult, male stumptailed macaques, ranging in age from 4 to 12 years, were divided into experimental groups; Vehicle (50/30/20% by volume of propylene glycol/ethanol/water) (three animals in the group), Compound of formula I-1% (three animals in the group), and Compound of formula I-5%(four animals in the group). The animals were kept in indoor group cages. Daily topical application of vehicle and drugs were made on the bald frontal scalp for 11 consecutive months. Conversion of vellus hairs to terminal hairs was evaluated from monthly photographs of the frontal scalp. The distribution of hair follicles between the phases of the hair cycle was determined by microscopic morphometry (folliculogram analysis) of the hair follicles in the biopsied scalp skin specimens at pretreatment (0), 6-month, and 11-month intervals. The results of photographic and folliculogram analysis are set forth in Tables I and II, respectively.

Experimental Procedure:

Vehicle (50/30/20% by weight of propylene glycol/ethanol/water);

Compound of formula I-1% in Vehicle;

Compound of formula I-5% in Vehicle.

0.5 ml of the above solutions were topically applied in an approximately 50 cm$^2$ area of bald scalp, once per day, 5 days per week for eleven consecutive months.

A) Photo Evaluation

Photographs of the frontal scalp were taken under anesthesia (ketamine HCl, 10 mg to 20 mg/kg), once per month for 11 months.

The extent of conversion from vellus hairs to terminal hairs is set forth in Table I.

TABLE I

| | Results |
|---|---|
| | Gross Photo Evaluation (at 11 months treatment) |
| Vehicle 1 | progression of baldness |
| Vehicle 2 | progression of baldness |
| Vehicle 3 | progression of baldness |
| Compound A$_1$ | very minimal effect |
| Compound A$_2$ | minimal effect |
| Compound A$_3$ | very minimal effect |
| Compound A$_4$ | minimal effect |

TABLE I-continued

| | Results |
|---|---|
| | Gross Photo Evaluation (at 11 months treatment) |
| Compound A$_5$ | moderate effect |
| Compound A$_6$ | minimal effect |
| Compound A$_7$ | moderate effect |

Compound A = 2-(6-cyano-3,4-dihydro-2,2-dimethyl-2H-1-benzopyran-4-yl)pyridine-1-oxide
A$_1$–A$_3$ = 1%
A$_4$–A$_7$ = 5%

B) Folliculogram Analysis:

This analysis determined the proportional number of hair follicles belonging to the different cyclic phases (telogen, early, Mid and late anagen, catagen), and the size (length) of each follicle in certain skin regions.

Methodology

A 4 mm punch skin biopsy was taken from the frontal scalp under anesthesia (ketamine) at 0,6 and 11 months after the beginning of treatment.

The Bouin-formalin fixed tissues were cut vertically to the epidermal surface parallel to the slant of the hair follicles. Serial paraffin sections (about 200 sections per sample with a thickness of 10 microns) were stained with hematoxylin and eosin.

Each serially cut section was projected with a micro projector onto thin tracing paper, and the entire outlines of epidermis and hair follicles, an average of 50, were traced on the paper and the cyclic phases, telogen (T), early to mid anagen (A$_3$), late anagen (A5), and catagen (C), and the size and length between the epidermal surface to the base of the hair follicles, were measured. The papers were projected on a brightly lighted screen and the number of different types of hair follicles and their lengths were recorded. The percentage of hair follicles in late anagen (A5) are set forth in Table II. See, Uno, H., *The Stumptailed Macaque as a Model for Baldness; Effects of Minoxidil,* International Journal of Cosmetic Science 8, 63–71 (1986) and Uno, M., et al., *Cyclic Dynamics of Hair Follicles and the Effect of Minoxidil on the Bald Scalps of Stumptailed Macaques,* The American Journal of Dermatopathology 7(3):283–297 p. 293 (1985).

TABLE II

| | Results | | |
|---|---|---|---|
| | Folliculogram Analysis % A5 | | |
| | 0 | 6 mos. | 11 mos. |
| Vehicle 1 | 14.8 | 11.7 | 18.8 |
| Vehicle 2 | 13.6 | 14.9 | 12.2 |
| Vehicle 3 | 10.8 | 34.1 | 29.5 |
| Compound A$_1$ | 6.7 | 9.1 | 39.1 |
| Compound A$_2$ | 28.6 | 10.6 | 27.3 |
| Compound A$_3$ | 6.7 | 24.2 | 26.2 |
| Compound A$_4$ | 23.3 | 40.4 | 22.0 |
| Compound A$_5$ | 17.6 | 21.4 | 30.6 |
| Compound A$_6$ | 6.8 | 14.5 | 25.5 |
| Compound A$_7$ | 5.4 | 12.5 | 14.7 |

Compound A = 2-(6-cyano-3,4-dihydro-2,2-dimethyl-2H-1-benzopyran-4-yl)pyridine-1-oxide
A$_1$–A$_3$ = 1%
A$_4$–A$_7$ = 5%

Creams, gels, solutions and shampoos containing ingredients set forth in the Examples below can be formulated by conventional means.

EXAMPLE 3
CREAM

| Ingredients | % w/w |
| --- | --- |
| 2-(6-cyano-3,4-dihydro-2,2-dimethyl-2H-1-benzopyran-4-yl)pyridine-1-oxide | 0.0005–5.0 |
| Cetyl Alcohol | 1.5 |
| Stearyl Alcohol | 2.5 |
| Sorbitan Monostearate (Span 60) | 2.0 |
| Mineral Oil | 2.0 |
| Glyceryl Monostearate and Polyoxyethylene Glycol Stearate Blend (Arlacel 165) | 4.0 |
| Polysorbate 60 (Tween 60) | 1.0 |
| Caprylic/Capric Triglyceride | 5.0 |
| Sorbitol Solution | 4.0 |
| Edetate Disodium | 0.1 |
| Butylated Hydroxyanisole (BHA) | 0.02 |
| Sorbic Acid | 0.2 |
| Potassium Sorbate | 0.1–0.2 |
| Water q.s. to | 100.00 |

EXAMPLE 4
GEL

| Ingredients | % w/w |
| --- | --- |
| 2-(6-cyano-3,4-dihydro-2,2-dimethyl-2H-1-benzopyran-4-yl)pyridine-1-oxide | 0.0005–5.0 |
| Butylated Hydroxyanisole (BHA) | 0.02 |
| Hydroxypropyl Cellulose | 3.00 |
| Ethyl Alcohol, 95% proof | 45.00 |
| Water q.s. to | 100.00 |

EXAMPLE 5
SOLUTION

| Ingredients | % w/w |
| --- | --- |
| 2-(6-cyano-3,4-dihydro-2,2-dimethyl-2H-1-benzopyran-4-yl)pyridine-1-oxide | 0.0005–5.0 |
| Propylene Glycol | 10.00 |
| Caprylic/Capric Triglyceride | 30.00 |
| Butylated Hydroxyanisole (BHA) | 0.02 |
| Ethyl Alcohol, Absolute q.s. to | 100.00 |

EXAMPLE 6
SHAMPOO

| Ingredients | % w/w |
| --- | --- |
| 2-(6-cyano-3,4-dihydro-2,2-dimethyl-2H-1-benzopyran-4-yl)pyridine-1-oxide | 0.0005–5.0 |
| Sodium $C_{14}$–$C_{16}$ Olefin Sulfonate | 15.00 |
| TEA Lauryl Sulfate | 10.00 |
| Lauramidopropyl Betaine | 10.00 |
| Cocamide DEA | 3.00 |
| Purified Water q.s. to | 100.00 |

I claim:

1. A method of promoting hair growth comprising topically administering to a host afflicted with androgenic alopecia an effective amount of the compound 2-(6-cyano-3,4-dihydro-2,2-dimethyl-2H-1-benzopyran-4-yl)pyridine-1-oxide.

2. The method of claim 1, wherein the compound 2-(6-cyano-3,4-dihydro-2,2-dimethyl-2H-1-benzopyran-4-yl)pyridine-1-oxide is administered in a topical composition comprising at least 0.0005% by weight of said compound and an inert dermatologically acceptable carrier.

3. The method of claim 2, wherein said topical composition comprises the compound 2-(6-cyano-3,4-dihydro-2,2-dimethyl-2H-1-benzopyran- 4-yl)pyridine-1-oxide in an amount of from about 0.0005% to about 5% by weight of the composition.

4. The method of claim 3, wherein said topical composition comprises the compound 2-(6-cyano-3,4-dihydro-2,2-dimethyl-2H-1-benzopyran- 4-yl)pyridine-1-oxide in an amount of from about 0.05% to 5% by weight of the composition.

5. The method of claim 4, wherein said topical composition comprises the compound 2-(6-cyano-3,4-dihydro-2,2-dimethyl-2H-1-benzopyran-4-yl)pyridine-1-oxide in an amount of from about 1% to about 5% by weight of the composition.

6. The method of claim 3, wherein said composition is a gel, cream, lotion, shampoo or solution.

7. A pharmaceutical composition for topical administration to the head of a host afflicted with androgenic alopecia comprising an amount effective to promote hair growth of the compound 2-(6-cyano-3,4-dihydro-2,2-dimethyl-2H-1benzopyran- 4-yl)pyridine-1-oxide and an inert dermatologically acceptable carrier.

8. The pharmaceutical composition according to claim 7, wherein the topical composition comprises at least 0.0005% by weight of the compound 2-(6-cyano-3,4-dihydro-2,2-dimethyl-2H-1-benzopyran- 4-yl)pyridine-1-oxide.

9. The pharmaceutical composition according to claim 8, wherein the topical composition comprises the compound 2-(6-cyano-3,4 -dihydro-2,2-dimethyl-2H-1-benzopyran-4-yl)pyridine-1-oxide in an amount of from about 0.0005% to about 5% by weight of the composition.

10. The pharmaceutical composition according to claim 9, wherein the topical composition comprises the compound 2-(6-cyano-3,4-dihydro-2,2-dimethyl-2H-1-benzopyran-4-yl) pyridine-1-oxide in an amount of from about 0.05% to about 5% by weight of the composition.

11. The pharmaceutical composition according to claim 10, wherein the topical composition comprises the compound 2-(6-cyano-3,4-dihydro-2,2-dimethyl-2H-1-benzopyran-4-yl) pyridine-1-oxide in an amount of from about 1% to about 5% by weight of the composition.

12. The pharmaceutical composition according to claim 9, wherein said composition is a gel, cream, lotion, shampoo or solution.

13. A method for increasing the rate of terminal hair growth comprising topically administering to a host afflicted with androgenic alopecia an effective amount of the compound 2-(6-cyano-3,4-dihydro-2,2-dimethyl-2H-1 -benzopyran-4-yl)pyridine-1-oxide.

14. The method of claim 13, wherein the compound 2-(6-cyano- 3,4-dihydro-2,2-dimethyl-2H-1-benzopyran-4-yl)pyridine-1-oxide is administered in a topical composition comprising at least 0.0005% by weight of said compound and an inert dermatologically acceptable carrier.

15. The method of claim 14, wherein said topical composition comprises the compound 2-(6-cyano-3,4-dihydro- 2,2-dimethyl-2H-1-benzopyran-4-yl)pyridine-1-oxide in an amount of from about 0.0005% to about 5% by weight of the composition.

16. A method for converting vellus hair to terminal hair comprising topically administering to a host afflicted with androgenic alopecia an effective amount of the compound 2-(6-cyano-3,4-dihydro-2,2-dimethyl-2H-1-benzopyran-4-yl)pyridine-1-oxide.

17. The method of claim 16, wherein the compound 2-(6-cyano-3,4-dihydro-2,2-dimethyl-2H-1-benzopyran-4-yl)pyridine-1-oxide is administered in a topical composition comprising at least 0.0005% by weight of said compound and an inert dermatologically acceptable carrier.

18. The method of claim 17, wherein said topical composition comprises the compound 2-(6-cyano-3,4-dihydro-2,2-dimethyl-2H-1-benzopyran-4-yl)pyridine-1-oxide in an amount of from about 0.0005% to about 5% by weight of the composition.

19. The method of claim 18, wherein said topical composition comprises the compound 2-(6-cyano-3,4-dihydro-2,2-dimethyl-2H-1-benzopyran-4-yl)pyridine-1-oxide in an amount of from about 0.05% to 5% by weight of the composition.

* * * * *

UNITED STATES PATENT AND TRADEMARK OFFICE
CERTIFICATE OF CORRECTION

PATENT NO. : 5,470,861
DATED : November 28, 1995
INVENTOR(S) : Charles Stanford Harmon It is certified that error appears in the above-indentified patent and that said Letters Patent is hereby corrected as shown below:

Column 8, Claim 7, line 32: " 1benzopyran" should read --- 1-benzopyran --- .

Signed and Sealed this

Nineteenth Day of March, 1996

Attest:

BRUCE LEHMAN

Attesting Officer      Commissioner of Patents and Trademarks